United States Patent [19]

Relenyi et al.

[11] Patent Number: 4,489,098

[45] Date of Patent: Dec. 18, 1984

[54] 2,2,3-TRIHALOPROPIONALDEHYDES AS ANTIMICROBIAL AGENTS

[75] Inventors: Attila G. Relenyi; George A. Paul, both of Midland, Mich.

[73] Assignee: The Dow Chemical Company, Midland, Mich.

[21] Appl. No.: 425,359

[22] Filed: Sep. 28, 1982

[51] Int. Cl.$^3$ ............................................. A01N 35/00
[52] U.S. Cl. ..................................................... 424/333
[58] Field of Search ........................................ 424/333

[56] References Cited

U.S. PATENT DOCUMENTS

| | | | |
|---|---|---|---|
| 2,665,217 | 1/1954 | Meuli | 99/154 |
| 3,493,658 | 2/1970 | Schmidt et al. | 424/267 |
| 3,582,463 | 6/1971 | Schwerdle | 424/333 |
| 3,608,084 | 9/1971 | Matt | 424/304 |
| 3,647,610 | 3/1972 | Wolf | 162/161 |
| 3,689,660 | 9/1972 | Burk et al. | 424/304 |
| 3,751,444 | 8/1973 | Solem et al. | 260/465.4 |
| 4,163,798 | 8/1979 | Burk et al. | 424/333 |

FOREIGN PATENT DOCUMENTS 2057407 5/1971 France.

OTHER PUBLICATIONS

Bitterfeld; Chemical Abstracts, vol. 76 (1972), 95751b.

*Primary Examiner*—Leonard Schenkman
*Assistant Examiner*—Joseph A. Lipovsky
*Attorney, Agent, or Firm*—Norman L. Sims

[57] ABSTRACT

The present invention is a method of treating an aqueous system to inhibit the growth of microorganisms therein which comprises adding to the aqueous system an effective amount of a 2,2,3-trihalopropionaldehyde.

7 Claims, No Drawings

2,2,3-TRIHALOPROPIONALDEHYDES AS ANTIMICROBIAL AGENTS

BACKGROUND OF THE INVENTION

The invention relates to a new method of inhibiting the growth of microorganisms in aqueous systems. More specifically, it relates to a method of using 2,2,3-trihalopropionaldehydes to inhibit the growth of microorganisms in aqueous systems.

Biofouling is a problem which attends many aqueous systems. For example, lagoons, lakes, ponds, pools, industrial wash water, cooling water and pulp and paper mill water all possess conditions which are conducive to the growth and reproduction of slime-forming microorganisms. In both once-through and recirculating cooling, for example, biofouling, such as slime production and algal matting, by microorganisms is an extensive and constant problem.

Airborne organisms are readily entrained in the water of cooling towers and find this warm medium an ideal environment for growth and multiplication. In the case of cooling towers, aerobic and heliotropic organisms flourish on the tower proper while other organisms colonize and grow in such areas as the tower sump, piping and passages of the cooling system. Such organisms produce a slime which deteriorates the tower structure in the case of wooden towers. In addition, the deposition of slime on metal surfaces promotes corrosion. Furthermore, slime carried through the cooling system plugs and fouls lines, valves, strainers, etc., and deposits on heat exchange surfaces. In the latter case, the impedence of heat transfer can greatly reduce the efficiency of the cooling system.

In pulp and paper mill systems, slime formed by microorganisms is also frequently and, in fact, commonly encountered. Fouling or plugging by slime also occurs in the case of pulp and paper mill systems. Microbial attack by either bacteria or fungi, or both, causes the loss of useful properties, foul odors, slime formation, slime spots in paper, reduced strength of paper, production down-time, and the possibility of skin infections in persons handling these materials.

As a result, extensive use is made of biocides in cooling water and pulp and paper mill systems. Materials which have enjoyed widespread use in such applications include chlorine, organo-mercurials, chlorinated phenols, organo-bromines and various organo-sulfur compounds. Other materials used as antimicrobials, especially as slimicides are halocyanoamides, in particular, 2,2-dibromonitrilopropionamide (DBNPA). See Nolan et al., U.S. Pat. No. 2,419,888; Schmidt et al., U.S. Pat. No. 3,493,658; Wolf, U.S. Pat. No. 3,649,166; and CIBA S.A., Belgian Pat. No. 668,336.

Another known antimicrobial compound is 2,3-dibromopropionaldehyde (see Schwerdle, U.S. Pat. No. 3,582,463, June 1, 1971, incorporated herein by reference). Both 2,3-dibromopropionaldehyde and 2,2-dibromonitrilopropionamide (DBNPA) are relatively unstable compounds which have a tendency to decompose in storage and in transit. The use of stabilizers to prevent this decomposition is often required. See Schwerdle, U.S. Pat. No. 3,582,463 and Burk et al., U.S. Pat. No. 4,163,798, Aug. 7, 1979 (incorporated herein by reference). These compounds are relatively ineffective in basic aqueous systems.

An antimicrobial compound which is relatively stable and is effective under basic conditions is desirable. Such an antimicrobial compound has been discovered.

SUMMARY OF THE INVENTION

The invention is a method of treating an aqueous system to inhibit the growth of microorganisms therein which comprises adding to the aqueous system an effective amount of a 2,2,3-trihalopropionaldehyde which can be represented by the formula

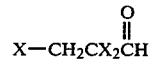

wherein X is separately in each occurrence bromine, chlorine, fluorine and iodine.

DETAILED DESCRIPTION OF THE INVENTION

It is preferable that X be the same halogen in each occurrence. Preferable halogens are chlorine and bromine. A most preferred 2,2,3-trihalopropionaldehyde is 2,2,3-tribromopropionaldehyde.

It has been discovered that these trihalopropionaldehydes are useful in inhibiting the growth of microorganisms in any aqueous system wherein the proliferation of microorganisms and by-products therefrom is a problem. For example, these compounds are useful in inhibiting the formation of slime in water cooling towers and in pulp and paper mills. Aqueous system as used herein refers to any water-containing environment subject to the growth of microorganisms.

The 2,2,3-trihalopropionaldehydes are used in amounts which are effective in inhibiting or controlling the growth or formation of microorganisms in the aqueous system to which they are applied. Such effective amount is dependent on the conditions of the aqueous system, for example, the presence of foodstuff for the microorganisms, water temperature, degree of aeration and pH, which affect microorganisms reproduction and vary from time to time and point to point in a particular system. Suitable amounts include between about 0.5 and 1000 parts per million parts of the aqueous system. Preferred amounts include between about 5 and 300 parts per million parts of the aqueous system, whereas between about 5 and 50 parts per million parts of the aqueous system are most preferred.

The method or place of addition may vary from system to system depending upon the conditions of that system. The 2,2,3-trihalopropionaldehydes may be added continuously or intermittently when needed. The place of addition may be at particular points, such as where the greatest concentration of microorganisms occur. Addition can also be done so as to allow even distribution throughout the entire system.

The 2,2,3-trihalopropionaldehydes demonstrate surprising stability and can be stored and transported without the use of stabilizers. These compounds also exhibit surprising stability in the presence of stainless steel which is often used in storage and transport tanks.

In basic aqueous systems 2,2,3-trihalopropionaldehydes are stable and exhibit much higher antimicrobial activity than other antimicrobial compounds. The 2,2,3-trihalopropionaldehydes can be used at a pH of between about 1 and 10, preferably between about 1 and 8.5.

A further advantage of these compounds is their biodegradable nature. These compounds are hydrolyzed by water and decompose after several weeks in an aqueous system. The rate of decomposition is much slower than the rate of inhibition of the growth of microorganisms in aqueous systems.

The trihalopropionaldehydes can be prepared by contacting three equivalents of halogen with acrolein with or without a suitable solvent. A suitable solvent is one which dissolves acrolein and does not react with the halogen, for example, chlorinated hydrocarbons such as dichloroethane, methylene chloride and 1,1,1-trichloroethane; ethers such as tetrahydrofuran and diethyl ether; and alkylene glycol monoethers. The addition of a halogen to acrolein is exothermic so it is advantageous to control the temperature of the reaction mixture by cooling or by the rate of addition of the halogen. The first two halogen atoms add to the acrolein quickly, whereas the third halogen atom adds slowly. In order to add the third halogen atom, the reaction mixture temperature should be elevated. Suitable temperatures for the addition of the third halogen atom are between about 50° C. and 100° C., more preferably between about 70° C. and 80° C.

SPECIFIC EMBODIMENTS

The following examples are included for the purpose of illustration and are not intended to limit the scope of the invention or claims.

EXAMPLE 1

Preparation of 2,2,3-Tribromopropionaldehyde

Bromine (54 ml, 1.03 moles) was added dropwise to a solution of acrolein (66.6 ml, 1.0 mole) in carbon tetrachloride (200 ml) over a 1.5-hour period. The solution temperature was maintained between 19° C. and 26.5° C. by controlling the rate of addition. Proton magnetic resonance analysis of the resultant red-brown solution revealed the absence of acrolein and the presence of 2,3-dibromopropionaldehyde. Another equivalent of bromine was quickly added and proton magnetic resonance analysis revealed formation of 2,2,3-tribromopropionaldehyde and water. The red solution was allowed to stir for three days. Thereafter the solution was stripped of volatiles to give 290.65 g (98 percent) of 2,2,3-tribromopropionaldehyde.

EXAMPLE 2

Preparation of 2,2,3-Tribromopropionaldehyde

Bromine (106 ml, 2.03 moles) was added dropwise to a solution of acrolein (66.6 ml, 1.0 mole) in carbon tetrachloride over a 4.5-hour period, to afford a red-brown solution. The temperature was maintained at between 20° C. and 27° C. Volatiles were removed by vacuum (25° C., 1.0–0.5 mm Hg) to give 293.60 g (99.69 percent) of 2,2,3-tribromopropionaldehyde.

EXAMPLE 3

Preparation of 2,2,3-Tribromopropionaldehyde

To a solution of acrolein (100.0 g, 1.78 moles) in dichloromethane (150 ml), bromine (571.2 g, 3.57 moles) was added in a dropwise manner over a two-hour period, to afford a red solution. The reaction temperature ranged from about 25° C. to 45° C. during the addition. Thereafter, the volatiles were removed to give 461.27 g (87.9 percent) of a yellow oil, identified as 2,2,3-tribromopropionaldehyde.

EXAMPLE 4

Preparation of 2,2,3-Tribromopropionaldehyde

Bromine (1.79 moles) was added in a dropwise manner over three hours to a solution of acrolein (100.0 g, 1.78 moles) in dichloromethane (150 ml). The addition of bromine was controlled to maintain the reaction solution at a temperature between 40° C. and 50° C. Thereafter the reaction solution was heated to 70° C. Then, bromine (285.8 g, 1.78 moles) was added to the solution in a dropwise manner over a four-hour period. The addition was controlled to maintain the solution temperature between 70° C. and 80° C. The solution was cooled to room temperature and the volatiles removed by evaporation to give a 99.4 percent yield of 2,2,3-tribromopropionaldehyde.

EXAMPLE 5

Preparation of 2,2,3-Tribromopropionaldehyde

Bromine (1142.0 g, 7.15 moles) was added in a dropwise manner over six hours to a solution of acrolein (200.0 g, 3.57 moles) in dichloromethane (300 ml). During the addition the temperature was between 35° C. and 67° C. The resultant dark yellow solution was evaporated of volatiles to give 1000 g of 2,2,3-tribromopropionaldehyde. This was a greater than 95 percent yield.

EXAMPLE 6

Preparation of 2,2,3-Tribromopropionaldehyde

Bromine (226.9 g, 1.42 moles) was added in a dropwise manner to a solution of acrolein (40.0 g, 0.71 mole) in 1,1,1-trichloroethane (100 ml) over fifty-five minutes. The addition was controlled to maintain the reaction solution at a temperature of 48° C. The resultant red solution was stripped of volatiles to give 208.84 g of 2,2,3-tribromopropionaldehyde, giving a 99.8 percent yield.

EXAMPLE 7

Antimicrobial Screening Data

| Microorganisms Tested | ATCC No. |
| --- | --- |
| Enterobacter aerogenes | 13048 |
| Pseudomonas aeruginosa | 15442 |
| Aspergillus niger | 16404 |
| Saccharomyces cerevisiae | 4105 |

*Enterobacter aerogenes* and *Pseudomonas aeruginosa* are bacteria. *Aspergillus niger* and *Saccharomyces cerevisiae* are fungi.

A 1.0M solution of tricine (17.9 g/l) in deionized water was prepared for use as an alkaline nutrient medium. The tricine was used as a buffer to maintain the pH of the alkaline nutrient medium. To a portion of the alkaline nutrient medium was added 1N NaOH to prepare a solution with a pH of 8.2. Such a solution with a pH of 6.8 was also prepared. Melted agar (100 g), nutrient for the microorganisms which were tested, was added to several glass Erlenmeyer flasks containing the alkaline nutrient medium and autoclaved at 15 psi for 15 minutes.

Solutions of 1.0 percent and 0.1 percent of 2,2,3-tribromopropionaldehyde, 2,2-dibromonitrilopropionamide and 2,3-dibromopropionaldehyde were made in acetone and water.

After autoclaving and cooling to about 48° C., various amounts of the above compounds were added to the several flasks so as to prepare flasks containing concentrations of 10, 25, 50, 100, 250 and 500 parts per million of each of the three compounds.

Three sterile petri plates for each concentration of each compound were prepared by pouring the solutions onto the plates. The plates were allowed to cool and solidify. Immediately after solidification, the agar surfaces were streaked with prepared suspensions of the test microorganisms.

The bacteria were tested at two pH levels, pH 6.8 and pH 8.2.

All plates were incubated at 30° C. The presence or absence of test bacteria growth was observed and recorded after 48 hours incubation. The observation for presence and absence of test fungus growth was made and recorded after 5 days incubation. All results were recorded as the highest level at which no growth occurs. If the highest level tested failed to inhibit the test microorganism, the result was recorded as >500 parts per million. The results for 2,2,3-tribromopropionaldehyde, 2,2-dibromonitrilopropionamide and 2,3-dibromopropionaldehyde are compiled in Table I.

TABLE I

| Test Organism | pH | ppm DBPA[1] for Inhibition | ppm DBNPA[2] for Inhibition | ppm TBPA[3] for Inhibition | ppm DBNPA[2] for Inhibition |
|---|---|---|---|---|---|
| Enterobacter aerogenes | 6.8 | 250 | 50 | 100 | 50 |
| Pseudomonas aeruginosa | 6.8 | 250 | 50 | 250 | 50 |
| Enterobacter aerogenes | 8.2 | >500 | >500 | 250 | >500 |
| Pseudomonas aeruginosa | 8.2 | 500 | >500 | 100 | >500 |
| Aspergillus niger | | 250 | 100 | 250 | 100 |
| Saccharomyces cerevisiae | | 100 | 50 | 50 | 25 |

[1]Dibromopropionaldehyde
[2]Dibromonitrilopropionamide
[3]Tribromopropionaldehyde Both dibromopropionaldehyde and tribromopropionaldehyde were compared side by side with dibromonitrilopropionamide in an identical set of experiments.

*Pseudomonas aeruginosa* is a bacterium which demonstrates broad spectrum resistance to biocides. The above tests show that 2,2,3-tribromopropionaldehyde inhibits the growth of this bacterium. It is widely believed that compounds which inhibit the growth of *Pseudomonas aeruginosa* are effective against most bacteria.

*Enterobacter aerogenes* is a bacterium which is considered to be one of the major causes of slime in coolant towers. This test shows that 2,2,3-tribromopropionaldehyde effectively inhibits the growth of this bacterium.

*Aspergillus niger* and *Saccharomyces cerevisiae* are fungi commonly found in coolant tower slime. It is believed that a compound which inhibits the growth of these fungi is a good slimicide. 2,2,3-Tribromopropionaldehyde demonstrates good activity in the inhibition of the growth of these fungi.

The above tests show that 2,2,3-tribromopropionaldehyde is a much better biocide than 2,3-dibromopropionaldehyde in basic systems.

What is claimed is:

1. A method of treating an aqueous system to inhibit the growth of microorganisms therein which comprises adding to the aqueous system an effective amount of a 2,2,3-tribromopropionaldehyde which can be represented by the formula

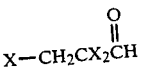

wherein X is bromine.

2. The method of claim 1 wherein the amount of the 2,2,3-tribromopropionaldehyde is between about 0.5 and 1000 parts per million parts of the aqueous system.

3. The method of claim 2 wherein the amount of the 2,2,3-tribromopropionaldehyde is between about 5 and 300 parts per million parts of the aqueous system.

4. The method of claim 1 wherein the microorganism is *Enterobacter aerogenes*.

5. The method of claim 1 wherein the microorganism is *Pseudomonas aeruginosa*.

6. The method of claim 1 wherein the microorganism is *Aspergillus niger*.

7. The method of claim 1 wherein the microorganism is *Saccharomyces cerevisiae*.

* * * * *